United States Patent [19]

Lichtenstein

[11] 3,946,731
[45] Mar. 30, 1976

[54] APPARATUS FOR EXTRACORPOREAL TREATMENT OF BLOOD

[76] Inventor: Eric S. Lichtenstein, 420 Taconic Road, Greenwich, Conn. 06830

[22] Filed: July 31, 1974

[21] Appl. No.: 494,006

Related U.S. Application Data

[63] Continuation-in-part of Ser. No. 395,214, Sept. 7, 1973, Pat. No. 3,912,455, which is a continuation-in-part of Ser. Nos. 108,118, Jan. 20, 1971, Pat. No. 3,774,762, and Ser. No. 157,942, June 29, 1971, abandoned.

[52] U.S. Cl. ..... 128/214 R; 23/258.5 R; 128/214 E; 128/DIG. 3; 210/87; 210/90
[51] Int. Cl.$^2$ .......................................... A61M 1/03
[58] Field of Search ......... 128/214 R, 214 B, 214 E, 128/214.2, DIG. 3, DIG. 13, 213; 23/258.5; 210/87, 90, 321

[56] References Cited
UNITED STATES PATENTS

| | | | |
|---|---|---|---|
| 2,721,732 | 10/1955 | Melrose | 23/258.5 |
| 3,416,664 | 12/1968 | Kumme et al. | 210/87 |
| 3,441,136 | 4/1969 | Serfass et al. | 210/90 |
| 3,511,238 | 5/1970 | Von Wrangell | 128/214 R |
| 3,513,845 | 5/1970 | Chesnut et al. | 23/258.5 |
| 3,533,408 | 10/1970 | Paoli | 128/214 R |
| 3,709,222 | 1/1973 | De Vries | 128/213 |
| 3,756,234 | 9/1973 | Kopp | 128/214 R |

Primary Examiner—Dalton L. Truluck
Attorney, Agent, or Firm—Blum Moscovitz Friedman & Kaplan

[57] ABSTRACT

An apparatus for extracorporeal treatment of blood can carry through automatically such functions as dialysis and oxygenation compensating, in the process, for changes in the condition of the patient. A fail-safe monitor receives signals from a number of sensors all of which must provide signals within acceptable ranges in order for the apparatus to continue to function. Deviation of a signal outside the corresponding acceptable range for longer than a preset period causes the fail-safe monitor to stop the flow of blood taken from the subject and to activate an alarm. The apparatus may be so constructed that the ducting through which blood and other fluids flow can be caused to act as valves and pumps by suitably applied pressure. Also, such portions of the apparatus can be made in a form which is sufficiently economical so that they can be regarded as disposable. The apparatus may be designed so that it can be programmed for specific patients and for treatment of specific conditions.

29 Claims, 10 Drawing Figures

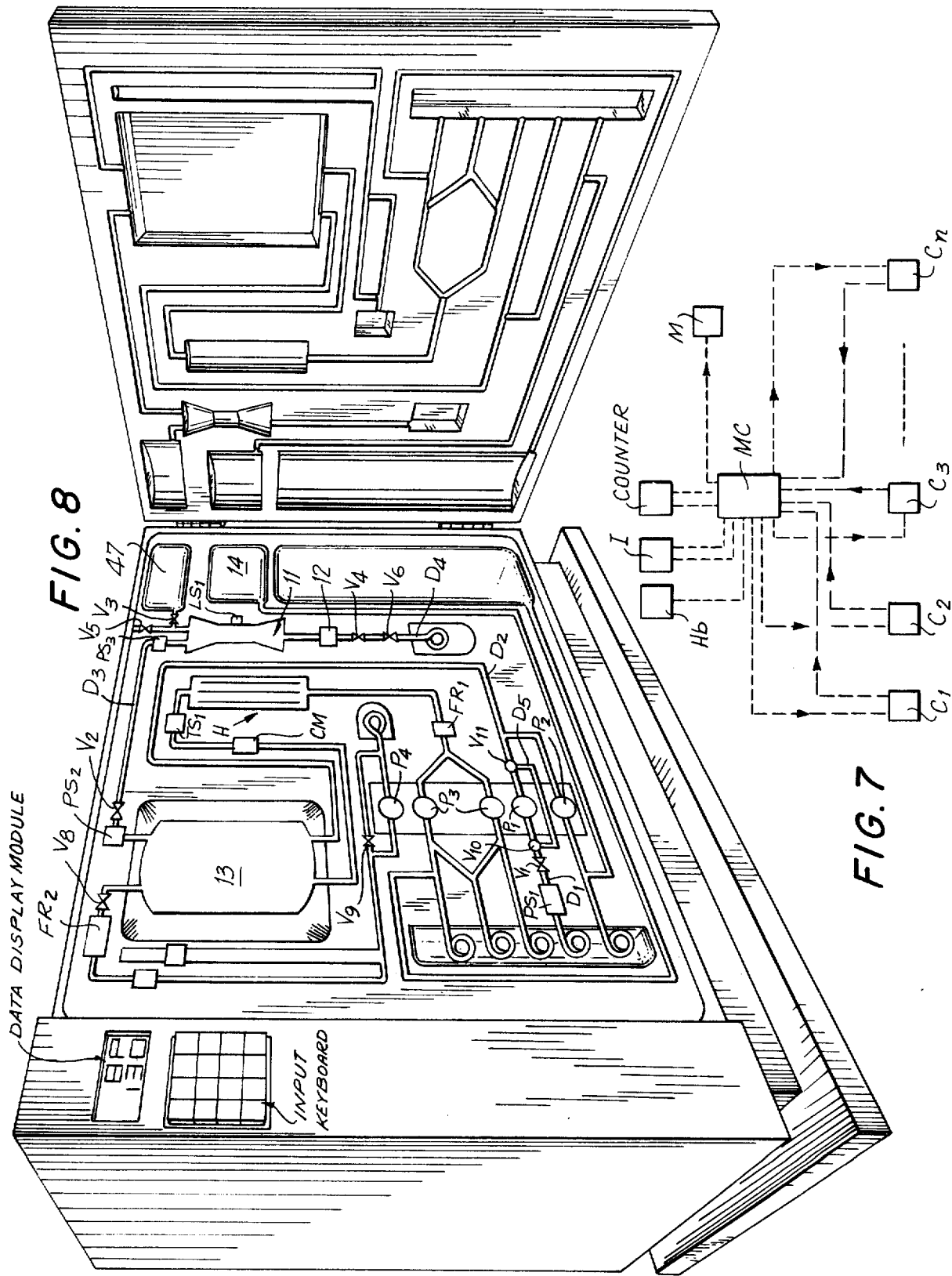

APPARATUS FOR EXTRACORPOREAL TREATMENT OF BLOOD

CROSS REFERENCE TO RELATED APPLICATION

The present application is a continuation-in-part of Ser. No. 395,214 filed Sept. 7, 1973, now U.S. Pat. No. 3,912,455 issued Oct. 14, 1975, itself a continuation-in-part of Ser. Nos. 108,118 filed Jan. 20, 1971 and 157,942 filed June 29, 1971, now abandoned. Ser. No. 108,118 issued as U.S. Pat. No. 3,774,762 on Nov. 27, 1973.

BACKGROUND OF THE INVENTION

The taking of blood from a subject for treatment and returning the blood to the subject requires control of a relatively large number of variables. Some of these are so critical that failure to control them adequately can result in death of the patient. As one of the simplest examples, the blood returning to the patient must be free of air bubbles. As another example, if the rate at which blood is being taken from the patient is such that there is an inadequate circulating blood volume, cardiovascular shock and death can result. Monitoring the patient's pulse rate and blood pressure, for example, allows anticipation of undesirable changes and the taking of appropriate compensating actions.

As aforenoted, the number of variables which must be monitored is such that extracorporeal treatment of blood, as exemplified by dialysis, has been almost prohibitively expensive. Much effort has already been expended in the attempt to decrease the cost of necessary equipment. The amount of supervision by technical personnel required, however, remains a major obstacle to utilization of this life-saving technique. This cost is principally due to the necessity for expert monitoring of the patient's condition. Also, the necessity of avoiding the dangers involved in passing blood from one patient through a system through which blood from another patient has passed, requires extensive cleaning procedures for contaminated hardware, and use of disposable equipment, again involving considerable expenditure of time by skilled personnel to perform the necessary steps preparatory to performing the procedure itself. For these reasons the need for automated, economical equipment is great. Moreover, the number of individuals capable of benefitting from extracorporeal treatments of blood is so great that not all can receive the required treatment unless suitable automatic equipment can be developed. Such equipment, preferably, should be automated to the point where self-treatment or markedly increased efficiency of existing treatment facilities and personnel can be anticipated.

It is recognized that the ultimate monitor must be human; the condition of the patient can vary so widely and in so many ways while under treatment that the judgment of skilled personnel must be available. However, once a set of conditions is selected within which the patient's condition and the patient's blood must be maintained, the task of determining whether the conditions are met can be turned over to a machine. Such a machine must be able to discriminate between a temporary deviation from set conditions, and must be able to apply corrective measures designed to bring said conditions within preselected limits. However, it is essential that when any significant variable deviates beyond preselected limits and when the corrective measures applied by the machine fail to bring said variable back to the appropriate range, the machine must then halt the circulation of blood for the protection of the patient and preferably should activate an alarm.

In view of the large number of individuals known to require treatment for such pathological conditions as uremia, and the potential for use of extracorporeal treatments of blood in other conditions, such as hypoxemia, intoxication and poisoning, there is a pressing need for improved treatment systems at substantially reduced cost per patient. Conventional apparatuses fail to meet these requirements.

SUMMARY OF THE INVENTION

In an apparatus for circulating and treating blood, the blood circuit must include a connection with the patient, a controllable-rate pump means, a treatment chamber, a bubble trap for eliminating the possibility of a gas bubble being transferred back into the patient and a connection for returning blood to the patient. Additional features for providing the required safety are a pressure sensor for determining the pressure in the blood stream immediately exterior to the patient in the absence of flow and during flow, a fail-safe monitor for receiving a signal from the pressure sensor and determining whether the pressure lies within a preselected range, fail-safe valves upstream and downstream from the treatment chamber, said valves closing when said fail-safe monitor receives a signal indicating that the blood pressure is outside the preselected range and a sensor for sensing and signalling the cardiovascular status of the patient, the fail-safe monitor also being sensitive to the signal emitted by this sensor. Additionally, the line blood pressure sensor is connected to a controller which controls the rate of flow of blood through the system by controlling the rate of operation of the pump. As aforenoted, the fail-safe monitor can be activated if the blood pressure either in the line or in the patient drops too low and remains low despite the application of corrective measures including slowing down the pump rate.

A further component of the blood circuit is an apparatus for supplying an anti-coagulant such as heparin where the ratio of anti-coagulant to blood is maintained at a preselected value which is independent of the flow rate of the blood.

In general, the pressure of the blood in the treatment chamber must be controlled within preselected limits. A pressure sensor is positioned to detect the pressure of the blood in the treatment chamber, this pressure sensor sending a signal to a controller which adjusts a valve downstream from the treatment chamber to hold the blood pressure therein within said desired limits. If the pressure in the chamber goes outside said preselected limits, it is provided that a signal will be sent to the fail-safe monitor which will shut down the blood-circulating system.

In the process of treating the blood, the treatment may be such that the volume of blood leaving the patient and being returned to the patient may differ. In general, the volume will decrease. This is particularly the case where the treatment consists of hemodialysis. In this form of treatment, water and metabolic waste are removed through a membrane in the treatment chamber. The valve which provides the resistance which maintains the blood pressure in the treatment chamber at the desired level also controls the rate of return of blood to the patient.

It is necessary that any gas evolved or introduced during the treatment be eliminated prior to returning the blood to the patient. For this purpose a bubble trap is inserted in the line. The bubble trap has therein a level-sensor which is connected to a controller which adjusts a valve downstream from the bubble trap to adjust the rate of flow when the level in the bubble trap deviates beyond preselected limits.

When the level falls below a preselected limit and remains below said limit despite gradual closure of said downstream valve saline solution is introduced by means of a controller. In the event that the level deviates beyond one of the limits and remains beyond the limit for a preset period despite corrective action, a signal is supplied to the fail-safe controller to shut down the system.

At least the ducting connecting the various parts of the blood-circulating system may be made of flexible tubing or of flexible plastic sheets sealed together in a pattern of channels and chambers. By means of one or more auxiliary sheets sealed together in appropriate patterns, pressure can be applied to the ducting between a first pair of sheets so that the effect is that of valving or pumping.

Where the apparatus is to be used for hemodialysis, means are provided for supplying premixed dialysate or for mixing concentrate and water and then supplying the mixture. The rate at which dialysate is supplied is fixed relative to the rate of blood circulation, within a range of ratios. During ultrafiltration water passes from the blood through a membrane and into the dialysate. Flow rate measurement means are provided both upstream and downstream of the blood-treatment chamber so that the rate of ultrafiltration may be monitored. Since the rate of ultrafiltration depends on the pressure difference across the membrane, means are provided for monitoring and controlling the pressure of dialysate in the treatment chamber. Again, when the pressure in the dialysate compartment of the blood-treatment chamber varies outside preselected limits, a signal is transmitted to the fail-safe monitor to shut the system down. The dialysate is heated before entering the blood-treatment chamber and the temperature of the dialysate entering the blood-treatment chamber is monitored both for controlling the transfer of heat to the dialysate and for activating the fail-safe monitor in the event of failure of the control system. The conductivity of the dialysate is similarly monitored as a means of determining the electrolyte concentration. Also, the dialysate leaving the blood-treatment chamber is monitored in order to make certain that no blood has leaked into same. This monitor as well as the conductivity monitor are also connected to the fail-safe monitor appropriately.

As is evident, adjustment can be provided for a number of the variables such as pressure difference in the blood-treatment chamber, the liquid level in the bubble trap and so forth. For these variables, a time delay can be provided so that the fail-safe monitor is not activated until after a preselected period has passed. However, in the event of a sudden drop in bubble trap fluid level beyond the preset safety limit, blood appearing in dialysate, or the cardiovascular status of the patient going outside preselected limits, the fail-safe monitor must act immediately. Consequently, there is a hierarchy of conditions or signals related to conditions as a result of which certain of these signals can override others. Thus, if the cardiovascular status of the patient goes outside absolute preset limits the system will shut down and emit an alarm signal. Smaller deviations can be compensated for by programmed adjustment of suitable related variables.

A principal feature in an embodiment of the invention is the construction of at least part of the ducting and, optionally, of pumps and treatment chamber, of materials such that pneumatic control can be applied, the combination of ducting and pneumatic controls and, optionally pumps, being in disposable form.

Accordingly, an object of the present invention is an apparatus for automatically circulating blood extracorporeally under conditions such that circulation of blood will be halted in the event that any of a number of selected variables deviates beyond preselected limits, thereby protecting the subject against harm.

Another object of the present invention is an apparatus for oxygenating blood extracorporeally under conditions such that the patient is protected from harm in the event that any of a number of variables deviates beyond preselected limits.

A further object of the present invention is an apparatus for carrying out hemodialysis in which the rate of ultrafiltration is controlled and monitored, and the transport of waste products out of the blood is controlled, and which provides the option of supplying dialysate in the form of a premixed composition or of mixing the composition from concentrate and an appropriate supply of water, and wherein the essential variables necessary for protection of the patient are monitored and provision is made for an alarm signal in the event that any of a number of crucial variables depart from a preselected range, the system being shut down simultaneously with signalling said alarm.

An important object of the present invention is an apparatus for extracorporeal circulation and treatment of blood wherein those portions which must be discarded subsequent to each use are of inexpensive construction and are therefore disposable.

Yet another object of the present invention is an apparatus for the extracorporeal treatment of blood wherein flexible ducting and pumps operable by pneumatic pressure are constructed of disposable flexible tubing and/or disposable flexible plastic sheets sealed together in appropriate patterns.

A significant object of the present invention is an apparatus for extracorporeal circulation and treatment of blood incorporating a fail-safe monitor for receiving signals from control members to indicate when said system should be shut down to prevent harm to a patient, said system further incorporating control members designed for holding a number of variables within preselected limits.

A vital object of the present invention is an apparatus for extracorporeal circulation of blood wherein control members are connected to a fail-safe member for conveying thereto signals arranged in a hierarchy of importance so that those most crucially associated with the well-being of the patient can override those of lesser importance, and wherein automatic compensation for variations in those parameters of lesses importance can be gauged by response to those parameters designated to be of greater significance to either the patient's well-being, primarily, or, secondarily, to continuation of the treatment procedure.

A primary object of the present invention is an apparatus for the circulation and extracorporeal treatment of blood requiring a minimum of attention by supervisory personnel.

Still other objects and advantages of the invention will in part be obvious and will in part be apparent from the specification.

The invention accordingly comprises the features of construction, combinations of elements, and arrangement of parts which will be exemplified in the constructions hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 7 indicates schematically a hierarchy of controllers; and

FIG. 8 is a perspective view of an apparatus in accordance with the present invention.

DESCRIPTION OF THE PREFERRED EMBODIMENTS

Figure 1:
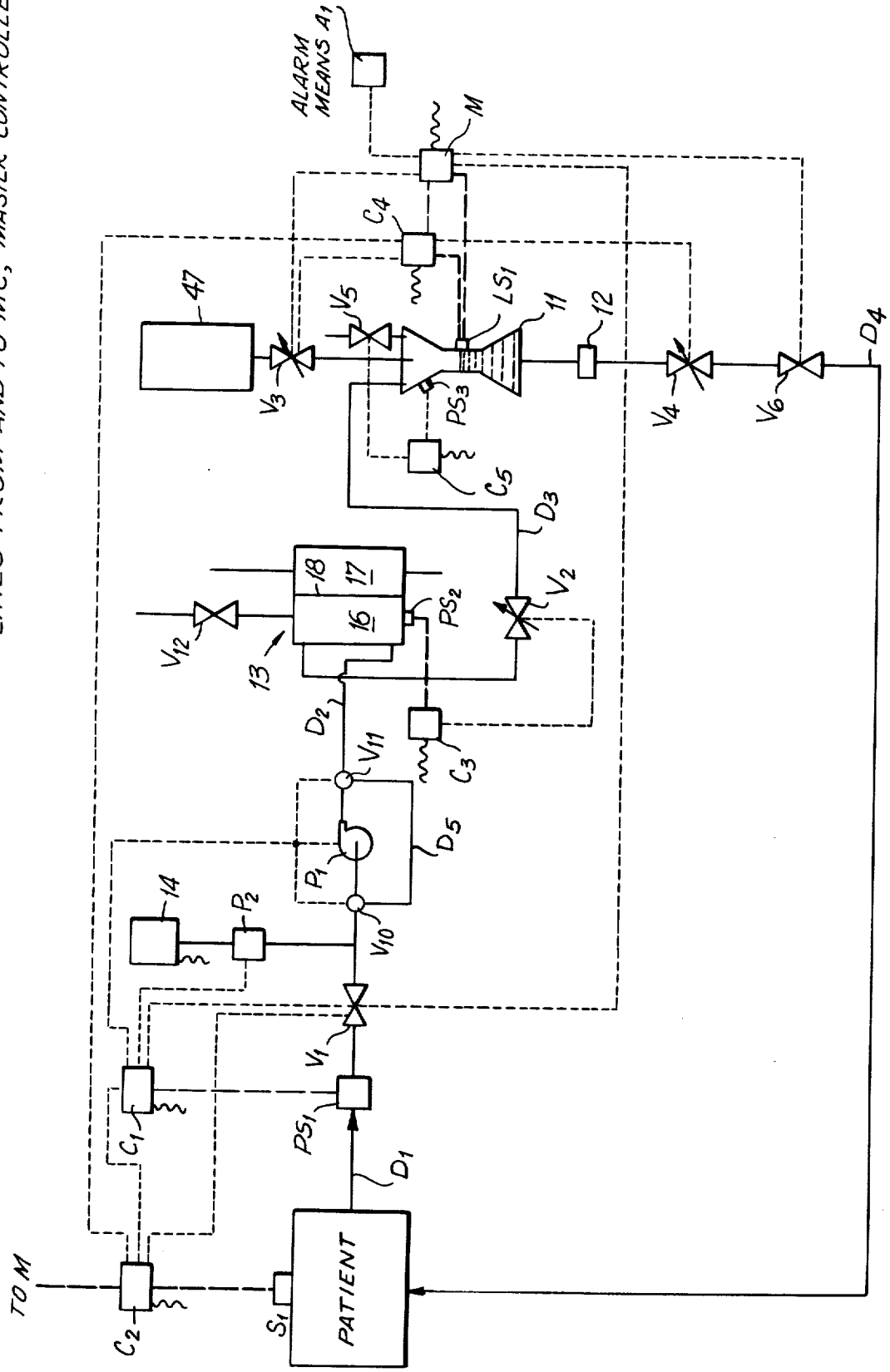
FIG. 1 shows schematically the apparatus in accordance with the present invention for circulating blood from a patient to a blood-treatment chamber and back to the patient again under fail-safe conditions.

A particularly convenient procedural step in preparation for drawing blood from a patient where the blood is to be treated extracorporeally is to establish surgically a channel between a neighboring artery and a vein thus enlarging and converting the adjacent venous channels into high pressure and high flow rate vessels. Such a channel, is termed an "A-V fistula." Vascular access for withdrawal of volumes of blood appropriate to extracorporeal circulation is accomplished by penetration through the skin into the enlarged venous channels with a hypodermic needle connected to appropriate tubing. A particularly appropriate region for such a fistula is the forearm. The pressure in the fistula is a variable largely dependent upon the patient's arterial blood pressure and to a lesser extent venous drainage. Fistula blood pressure is, therefore, one of the crucial variables in controlling the rate at which blood is taken from the patient. As is evident, blood must not be taken at such a rate that the patient's blood vessels collapse. Consequently a minimum blood-pressure in the fistula may be preselected and a control system organized around the criterion that the pressure in the fistula must not be allowed to fall below said preselected value. Moreover, for a blood-circulating system to be satisfactory, it is not enough that the system should be shut down when the pressure in the fistula drops below said preselected value. In addition, the capacity to adjust the rate of flow to fulfill the objective of holding the blood-pressure in the fistula within preselected limits must also be a feature of the system. This will enable an automatic compensation for variation in arterial pressure as reflected in mean fistula pressure allowing both continuous dialysis for a specifiable time, and automatic compensation for decreases in patient's blood pressure as reflected in the fistula blood pressure.

In view of the fact that the safety of the patient must take precedence over all other considerations, the conditions under which extracorporeal circulation of the blood takes place must predominate over consideration of the treatment to which the blood is subjected. In order to focus attention on the primary importance of the blood-circulating system itself, this system is shown separately in FIG. 1. Blood from the patient is taken through duct $D_1$, pump $P_1$, duct $D_2$, treatment chamber 13, duct $D_3$, bubble trap 11, blood-clot filter 12 and duct $D_4$, and thence back to the patient, the blood being introduced into the patient at a vein by means of a hypodermic needle (not shown).

The pressure in duct $D_1$ is determined by pressure sensor $PS_1$. When blood is flowing through the system, the pressure in $D_1$ will be different from that in the fistula of the patient, there being necessarily a pressure drop in the hypodermic needle connecting with the fistula and in $D_1$ upstream from $PS_1$. The pressure as determined by sensor $PS_1$ during flow is indicative of the pressure in the fistula but is not exactly the same, and for optimum protection of the patient it is necessary that means be provided for determining, periodically, the pressure in the fistula. In order to carry out this determination, the flow of blood through the system must be halted periodically. A convenient arrangement for effecting this purpose is a pair of 3-way valves $V_{10}$ and $V_{11}$ at the intake and delivery ends, respectively, of pump $P_1$, and $V_{10}$ and $V_{11}$ being connected by duct $D_5$ externally to pump $P_1$ and being under control of controller $C_1$. Rotating valve $V_{10}$ and valve $V_{11}$ so that the pump circulates blood through bypass duct $D_5$ rather than from duct $D_1$ into $D_2$, makes it possible to halt the flow of blood through the system for a short period of time without halting pump $P_1$.

While the flow of blood through the system is halted, there is, of course, no pressure drop between the fistula of the patient and sensor $PS_1$ in duct $D_1$. Consequently, sensor $PS_1$ then reads the blood-pressure in the fistula of the patient. The information as to the instantaneous value of the blood pressure in $P_1$ as read by sensor $PS_1$ is sent in the form of an appropriate signal to controller $C_1$. In the Figures referred to herein, long-dashed lines are used to indicate signals from a sensor to a controller and short-dashed lines are used to indicate signals from a controller to a controlled device, such as a valve, for instance.

In preparing the blood-circulating system for operation with a patient, a technically-trained individual, such as a physician, establishes preselected pressure limits beyond which the pressure in $D_1$ should not be allowed to vary. In the event that the pressure in $D_1$ moves toward either of the preselected limits, controller $C_1$ is programmed to change the pumping rate of pump $P_1$ in the appropriate direction. Alternatively, valve $V_1$ may be an adjustable valve, the resistance of which to flow of blood therethrough may be varied so as to keep the pressure upstream therefrom within said preselected limits. However, preferably, valve $V_1$ is a normally closed valve which requires a signal from $C_1$, stating, in effect, that the pressure as read by $PS_1$ is within said preselected limits, to hold said valve $V_1$ open.

As a further means of protecting the patient, the cardiovascular status of the patient may be continuously monitored as indicated schematically in FIG. 1 by sensor $S_1$. The variables monitored may include the patient's pulse rate, (optionally from electrocardiogram), and blood pressure at various sites, among others. Signals from $S_1$ are then transmitted to controller $C_2$ which also can shut down valve $V_1$ in the event that $S_1$ determines the patient's cardiovascular status to be unsuitable for the circulation of blood extracorporeally.

As is well known, when blood is taken from the body, it tends to coagulate. In order to prevent such coagulation, an anti-coagulant such as heparin may be supplied from a reservoir 14 into duct $D_1$. The flow rate $F_1$ of anti-coagulant from reservoir 14 is preferably held at a fixed ratio to the flow rate $F_2$ of blood. In other words, $F_1/F_2$ is held at or near a fixed preselected value. Anti-coagulant may be taken from reservoir 14 by means of gravity and flow rate $F_1$ controlled by means of an adjustable valve (not shown) set by $C_1$. Alternatively, pump $P_2$, the rate of which may be controlled by $C_1$, may be used to hold ratio $F_1/F_2$ within preselected limits.

Blood flowing through duct $D_2$ is carried to a blood treatment chamber indicated generally by the reference numeral 13. The pressure in compartment 16 is a critical variable with respect to the treatment to which said blood is to be subjected. For this reason pressure sensor $PS_2$ is provided for monitoring the pressure within compartment 16. Blood treatment chamber 13 is shown, arbitrarily, as being divided into two compartments 16 and 17 but such is not necessarily the construction of chamber 13. However, the division of blood-treatment chamber 13 into two compartments by means of a membrane 18 is a convenient arrangement for hemodialysis as will be detailed below. Taking hemodialysis as an example, the pressure difference maintained between compartments 16 and 17 is critical for controlling the rate of ultrafiltration. Consequently, means must be provided for holding the pressure in compartment 16 within preselected limits. Such means are constituted by controller $C_3$ receiving the pressure signal from sensor $PS_2$ and adjustable valve $V_2$ which is set by controller $C_3$. A major advantage of the present invention is that the combination of adjustable-rate pump $P_1$ with adjustable valve $V_2$ makes it possible to control both the blood-flow rate $F_2$ and the pressure in treatment compartment 16 without affecting adversely the pressure upstream from pump $P_1$ and, thereby, the pressure in the fistula of the patient.

The circulating blood is carried by duct $D_3$ to bubble-trap 11 fitted with level sensor $LS_1$ and pressure sensor $PS_3$. Again, pressure and level limits are preselected for bubble trap 11. The bubble trap is so shaped that it has a narrow section proximate the middle thereof, the purpose being to provide maximum change in level for a given change in volume of blood within the trap. Such an arrangement provides maximum sensitivity for monitoring and controlling the level of blood within the trap. When the level of blood within the trap moves toward either of the preselected limits, the change is monitored by level sensor $LS_1$ and the information conveyed to controller $C_4$. Controller $C_4$ adjusts variable valve $V_4$ to hold the level of blood within trap 11 and within said preselected limits.

Controller $C_4$ is so selected that if the blood level deviates beyond either of the preselected limits and remains beyond said limits for more than a preselected period of time, then a signal will be provided to fail-safe monitor M which will shut down valve $V_6$ in duct $D_4$, as well as pump $P_1$ and valve $V_1$, thereby terminating flow of blood in the system. Preferably, fail-safe monitor M will also carry out other functions, such as the addition of saline solution from reservoir 47 through valve $V_3$ to make certain that no gas can enter duct $D_4$. Further, fail-safe monitor M, desirably, activates alarm means $A_1$ for the purpose of summoning a competent attendant. It will be noted that controller $C_2$ which receives signals concerning the cardiovascular status of the patient is also connected to fail-safe monitor M, thereby providing for shutting down valves $V_1$ and $V_6$ and activating alarm means $A_1$ in the event that such action is warranted by the condition of the patient.

It has already been noted that valve $V_1$ is preferably of the normally-closed type, requiring a signal to keep it in open position. The same is true for valve $V_6$. The signal, for instance, may be electric as when a solenoid is used to hold the valve open against the biasing action of a spring, or maybe pneumatic, in which case a piston (not shown) holds the valve open against biasing action. Such an arrangement has the advantage that in the event of failure of power, the system automatically shuts down. The alarm means $A_1$ may also be constructed so that it requires a signal to keep it in the inactive state. So that alarm means $A_1$ may function if power is cut off, a reserve tank of pressurized gas or a storage battery may be suitably connected to said alarm means to activate same under such conditions.

It will be noted that fail-safe monitor M can be caused to close valves $V_1$ and $V_6$ and activate alarm means $A_1$ by either of controllers $C_2$ or $C_4$. Monitor M may also be made subject to a signal from controller $C_1$ informing monitor M as to whether the pressure in duct $D_1$ is within preselected limits, but, ordinarily, this is not necessary. Also, pressure sensor $PS_3$ which monitors the gas pressure in bubble trap 11 supplies a signal to controller $C_5$ to indicate when the gas pressure in bubble trap 11 rises beyond a preselected value. When such is the case, valve $V_5$ is opened for a period long enough to vent enough gas to drop the pressure in bubble trap 11 below the preselected upper limit. If desired, a signal can be taken from $C_5$ to activate M in the event that the pressure in bubble trap 11 rises so high that valve $V_5$ cannot cope with the pressure rise. However, such a situation is unlikely, and, in general, it is unnecessary to connect $C_5$ with M.

The construction of M is essentially that of an AND-gate which may be connected to any number of control devices all of which must send a signal indicating that the conditions which they are monitoring are within preselected ranges in order to prevent control M from shutting down the system. Additional variables monitored through intermediate controllers will be presented with respect to blood-treatment systems.

Oxygenation of the blood can readily be carried out with the present apparatus with addition of an anti-foaming system (not shown). In a first embodiment oxygen may be introduced through valve $V_{12}$ directly into the blood in blood compartment 16. In a second embodiment membrane 18 is permeable to oxygen, the oxygen being introduced into compartment 17.

The bubble trap 11 is particularly important where oxygen is introduced directly into the blood as in the first of the aforenoted embodiments. Obviously, some portion of the oxygen may not dissolve in the blood and this portion must be separated from the blood in order to avoid embolism.

The first of the embodiments is also suitable for intravenous alimentation or introduction of medicaments through valve $V_{12}$.

Figure 2:
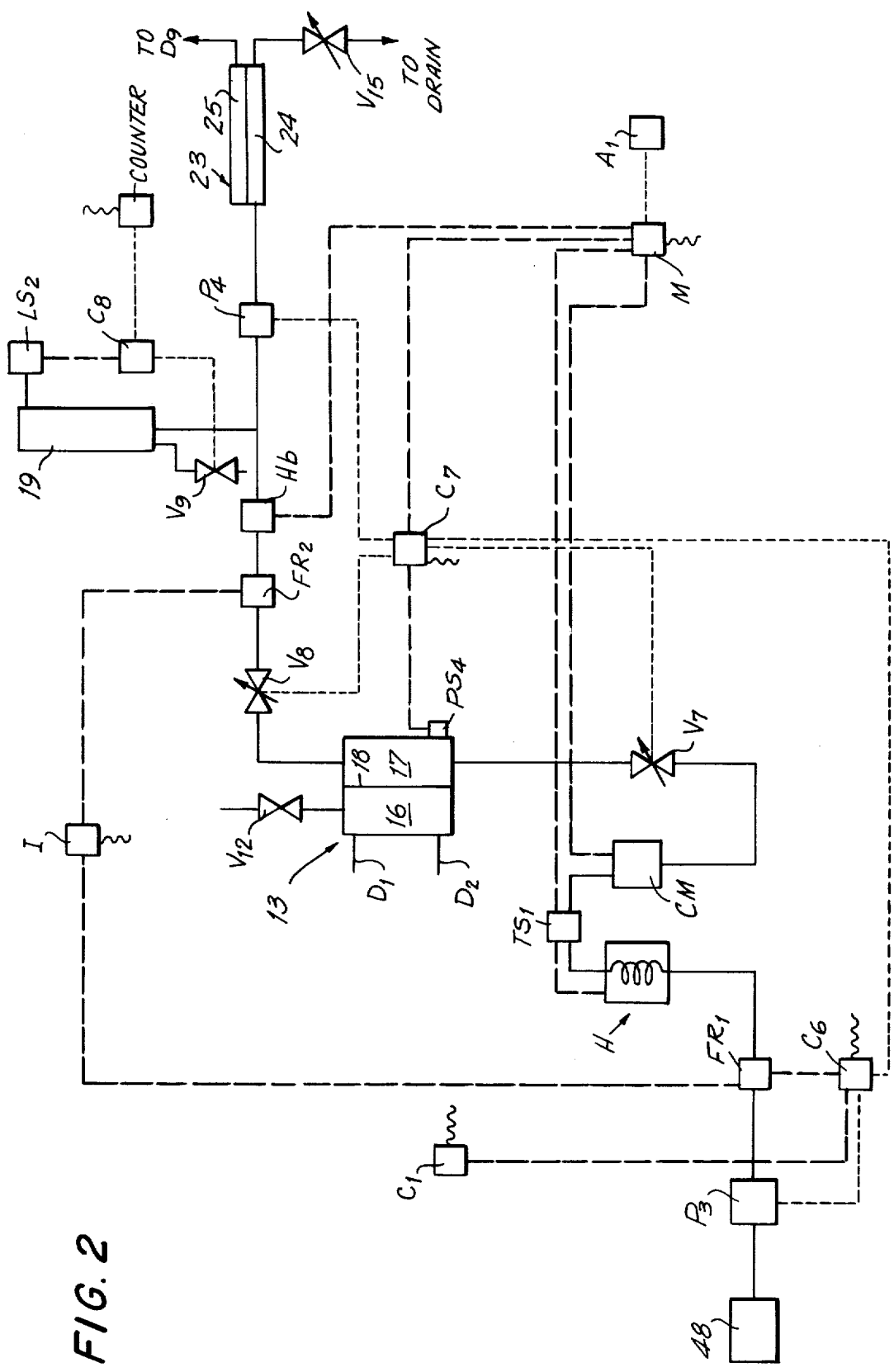
FIG. 2 shows schematically the apparatus in accordance with the present invention for hemodialysis, said apparatus to be used in combination with that shown in FIG. 1.
Figure 3:
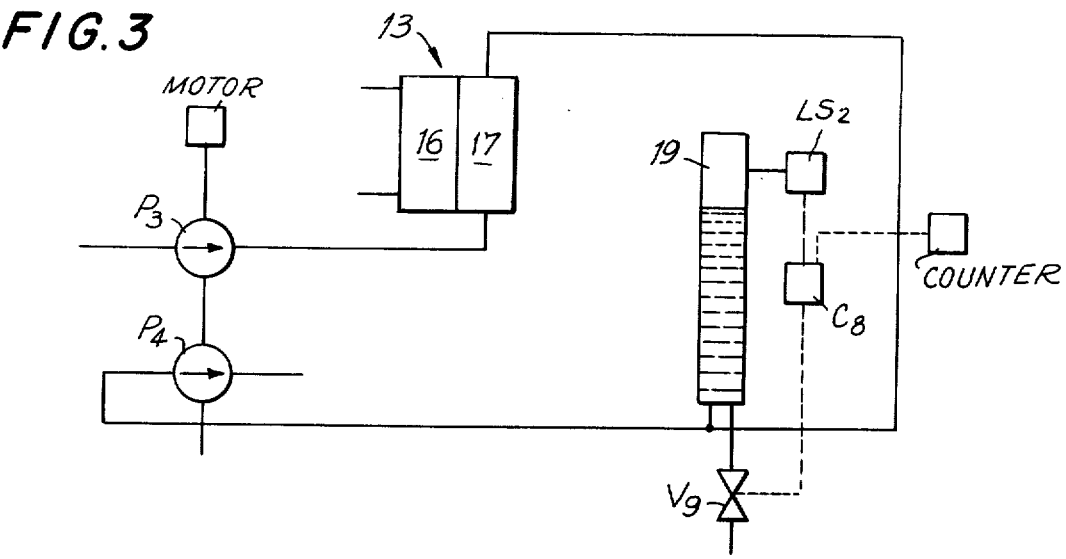
FIG. 3 shows schematically a system for monitoring and controlling the rate of ultrafiltration during hemodialysis.

An embodiment of the apparatus suitable for hemodialysis is shown in FIG. 2. FIG. 2 is to be read in conjunction with FIG. 1 and shows only those parts of the blood circulation system of FIG. 1 with which the dialysate-transfer system of FIG. 2 must coact.

Dialysate transfer means $P_3$, which, preferably, is a pump of controllable rate, transfers dialysate from dialysate supply 48 through flow rate sensor $FR_1$. Flow rate sensor $FR_1$ monitors the flow rate and supplies information to controller $C_6$ which controls the operation of $P_3$ to control the flow rate $F_3$ of dialysate. At the discretion of the operator, the ratio of $F_3$ to the blood flow rate, $F_2$, may be set at a desired level. To maintain this level, information as to the bloodflow rate is transferred from controller $C_1$ to controller $C_6$, the latter then adjusting the operating rate of $P_3$ to hold the ratio of $F_3$ to $F_2$ constant.

The dialysate is brought up to blood temperature in heater H and the temperature of the blood leaving heater H is monitored by temperature sensor $TS_1$. In the event that the temperature of the blood deviates beyond preselected limits, $TS_1$ signals fail-safe monitor M with which it is connected to shut down the system.

The conductivity of the dialysate is measured by conductivity meter CM. This is necessary to insure that the salt content of the dialysate is correct. Again, conductivity meter CM is connected with monitor M for shutting down the system in the event that the conductivity level passes beyond preselected levels.

Before entering dialysate compartment 17 of blood-treatment chamber 13, the dialysate passes through adjustable valve $V_7$. The purpose of valve $V_7$ is to make it possible for compartment 17 to be operated at subatmospheric pressure without causing interference with the operation of that portion of the dialysate system upstream from valve $V_7$. Operation at sub-atmospheric pressure may be necessary in order to establish the requisite pressure difference across semipermeable membrane 18, such a pressure difference being necessary to provide the desired rate of ultrafiltration in blood-treatment chamber 13. In view of the fact that both sub and super atmospheric pressure operations may be necessary, blood-treatment chamber 13 may be in the form of a canister, referred to as a dialyzer canister.

The pressure in dialysate compartment 17 is monitored by pressure sensor $PS_4$, the output signal of which is passed to controller $C_7$. Controller $C_7$ adjusts valve $V_7$ so as to permit the desired flow rate through the system while establishing the desired pressure difference between compartments 16 and 17. Pump $P_4$ in the dialysate line downstream from compartment 17 is under the control of controller $C_7$ and operates to drop the pressure in compartment 17 below atmospheric when necessary. Adjustable valve $V_8$, under the control of controller $C_7$ provides the necessary resistance to flow for holding the pressure in compartment 17 at the desired level. In the event that the pressure in compartment 17 deviates beyond preselected limits, $C_7$, operatively connected with monitor M shuts the system down. A detector Hb is also associated with the dialysate line downstream from compartment 17. In the event that a break occurs in membrane 18 so that blood enters the dialysate line 17, detector Hb detects the presence of blood such as by the change in color and transmits a signal to monitor M which shuts down the system.

The volume of fluid entering compartment 17 is measured by sensor $FR_1$. Since ultrafiltration is taking place in canister 13, the volume of fluid leaving compartment 17 is greater than that entering. Flow rate monitor $FR_2$ determines the flow rate of the fluid leaving the compartment and transmits the information to integrator I which also receives similar information from sensor $FR_1$. Integrator I measures the difference between the two flow rates and integrates this difference as a function of time, so that the total volume of water removed from the blood at any given time can be determined. Moreover, integrator I may be so constructed as to show the instantaneous difference between the upstream and downstream flow rates so that the instantaneous rate of removal of water can be determined.

Means for determining the integrated volume of ultrafiltrate removed at any time must be coordinated with means for providing the necessary dialysate system pressure changes and flows. A preferred method is to drive $P_3$ and $P_4$ synchronously so that they pass equal volumes of fluid per unit of time. The excess fluid arriving at $P_4$ then backs into chamber 19. The level of dialysate in chamber 19 rises until it reaches level sensor $LS_2$. Level sensor $LS_2$ transmits a signal to controller $C_8$ which in turn opens dump valve $V_9$ rapidly emptying chamber 19. Controller $C_8$ also sends a signal to a counter which totals the number of times that the chamber 19 has been filled and empties. The volume of 19 being known, the information supplied by the counter makes it possible to calculate the total volume of fluid dialyzed up to any given point. As is evident, the counter could be so constructed as to carry out the calculation. Chamber 19 may either have a vent (not shown) or may be collapsible, so that no vent is needed. This latter form is particularly suitable where chamber 19 is formed as part of a heat-sealed or cemented pattern between a pair of flexible plastic sheets. Means for determining the increase in volume of dialysate resulting from hemodialysis have been described in my U.S. Pat. No. 3,774,762. Increase in pressure in a reservoir can also be used as means of delivering accumulated volume.

Dialysate, after leaving $P_4$, normally is discharged to waste. Under certain circumstances, it may be desirable to recover a portion of the water in the dialysate. Such circumstances may arise when the system is designed to be portable. In that case the dialysate leaving $P_4$ is taken to water separator means 23. The water removed from the dialysate is returned to duct $D_9$ (FIG. 6) at which point it can be used for mixing with fresh dialysate concentrate. The water separator means 23 is preferably a reverse-osmosis canister. The water separated off may contain some salt but is essentially free of organic waste products. Pump $P_4$ generates the needed pressure difference, valve $V_{15}$ providing the necessary outflow resistance. The concentrated dialysate containing waste products removed from the patient's blood stream flows through $V_{15}$ to a drain.

As aforenoted, it is convenient to drive pumps $P_3$ and $P_4$ synchronously and in preselected ratio to $P_1$ and $P_4$, as determined by the rate of $P_1$, set by controller $C_1$. This may readily be done by using a single motor or other motive means to drive all pumps. In a convenient form all pumps consist of flexible tubing sequentially compressed by moving fingers or rollers driven by single motor. Such devices are widely available and can be used for driving a multiplicity of pumps, using a separate flexible tube for each fluid transfer line. Desired, that is, selected flow rate ratios may be established by use of tubing of different sizes for the different flow lines. When such a device is used $P_1$, $P_2$, $P_3$ and $P_4$ (see FIG. 8) will all be driven by the same motive means, using properly-sized tubing for each line to establish the desired flow ratios. Such devices are of the positive-displacement type so that the various adjustable valves in the system, for the most part, do not control flow rate but rather, provide pressure differences.

As aforenoted, when circulating blood extracorporeally and treating same, the status of the patient must be continuously monitored. If the blood pressure of the patient drops to a value considered unsuitable, despite the automatic compensation systems and adjustment of ultrafiltration rate, then controller $C_2$ can be called into play to add saline, to increase the patient's intravascular volume, from reservoir 47 through adjustable $V_3$ to bubble trap 11. In the event that sensor $S_1$ discovers that the patient's pulse rate is rising, without a detectable decrease in blood pressure, it is generally necessary that the rate of ultrafiltration be decreased. This can be effected by transmitting a signal from $C_2$ to $C_1$ to decrease the pump rate of $P_1$, and thereby the pressure in compartment 16 or by decreasing the pressure difference across membrane 18.

It will be realized that the particular combination of sensors, controllers, pumps, adjustable valves and two-position valves is essentially arbitrary in that the controllers, particularly, can be increased or decreased in number depending upon the way in which they are constructed. The essential point is that it must be possible to control flow rate through the blood circulating system, flow rate through an auxiliary system such as a dialysate system, pressure drop across a membrane, volume of fluid in the system and temperature of dialysate. In addition, it is necessary that means be provided in the form of a fail-safe monitor which can shut down the system safely in the event that any crucial variable takes on a value outside preset limits.

Figure 4A:
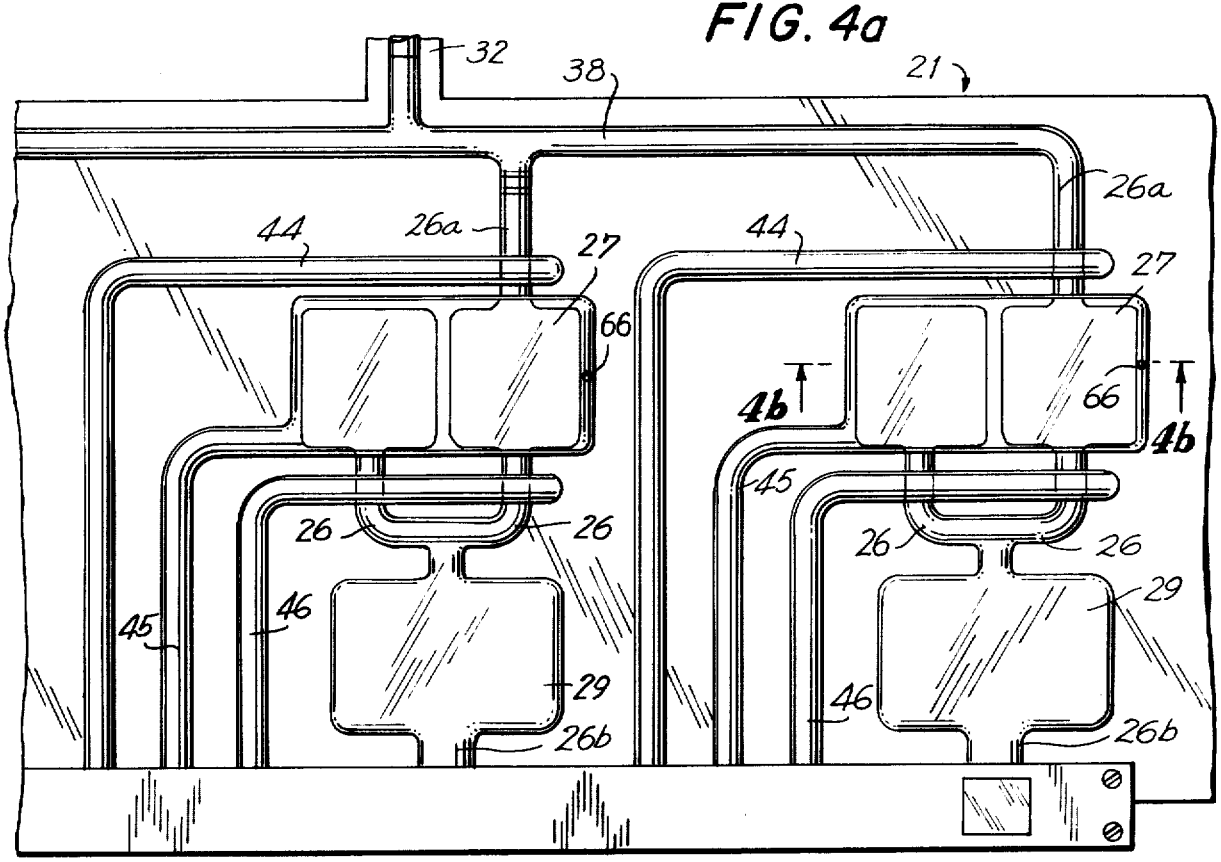
FIGS. 4a and 4b show in plan and cross-section respectively, ducting and pumps of flexible plastic sheet sealed in appropriate patterns for pneumatic operation.
Figure 4B:
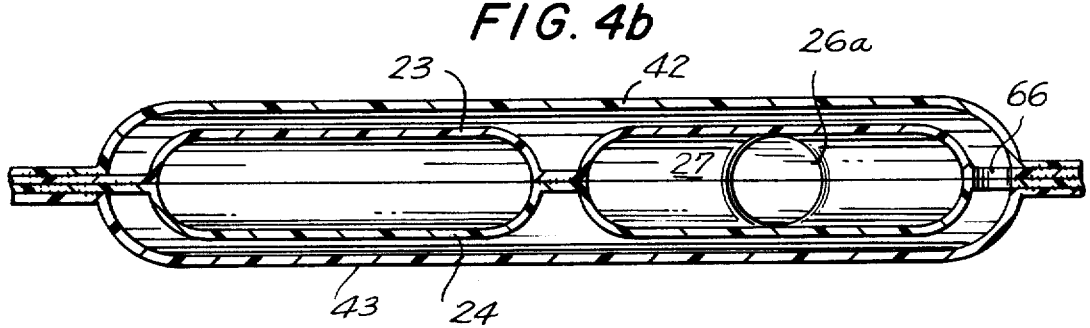

As aforenoted, it is desirable that substantial portions of the apparatus described herein be disposable. In my application having the Ser. No. 395,214 and filed on Sept. 7, 1973, I have described how a plastic sheet system sealed together in appropriate patterns may be used as ducting and may be manipulated to perform the functions of both valves and pumps. Referring now to FIGS. 4a and 4b, fluid enters plastic sheet portion 21 of the apparatus through duct 32 formed by heat sealing or cementing between two sheets of flexible plastic, these sheets, preferably, being transparent. The fluid passes through duct 26a also formed by sealing the two sheets of plastic together and into chamber 27. However, chamber 27 is formed between what may be termed a "primary" pair of plastic sheets 23 and 24 between which are also formed ducts 38, 26a and 26b. At least a third sheet, 42, is sealed to the primary sheets as shown in FIG. 4b. If duct 44, formed between topmost sheet 42 and sheet 23 is pressurized sufficiently, either by liquid or gas, duct 26a will be closed off. Moreover, by varying the extent of pressurization of duct 44, the combination of duct 44 overlying duct 26a functions as an adjustable valve. At full pressurization of duct 44 duct 26a is closed off completely.

When duct 44 is unpressurized, fluid may be introduced through duct 26a into chamber 27. It will be assumed, for the moment, that duct 46 is pressurized completely so that the combination of duct 46 and duct 26 acts as a valve. Now, if duct 46 is vented and duct 45 is sufficiently pressurized, the space between sheet 42 and sheet 23 will be pressurized to any extent commensurate with the strength of the system, whereupon the combination of sheet 42 and chamber 27 formed between sheets 23 and 24 act as a pump for displacing liquid through duct 26 into chamber 29. In a preferred form, a fourth sheet 43 is placed on the opposite side of chamber 27 from sheet 42. So that the pressure both above and below the chamber 27 may be equal, sheets 23 and 24 are perforated as shown at 66 in FIG. 4b.

From the above description it will be seen that a system of three, and preferably four flexible plastic sheets can function as a pneumatic or hydraulic system containing ducting, adjustable valves and adjustable rate pumps. Of course, the pumping action is pulsating rather than continuous, but allowance can be made for this feature by providing expansion or flow-equalization chambers. The significant feature of this type of arrangement is that the flexible sheets of which the device is formed can be assembled automatically into any desired pattern. Since the cost of the material and the cost of assembly are low, the system is disposable, making it possible to provide a new pneumatic system for each successive patient so that it is unnecessary to risk the danger of contamination, etc., involved in re-use.

Figure 5A:
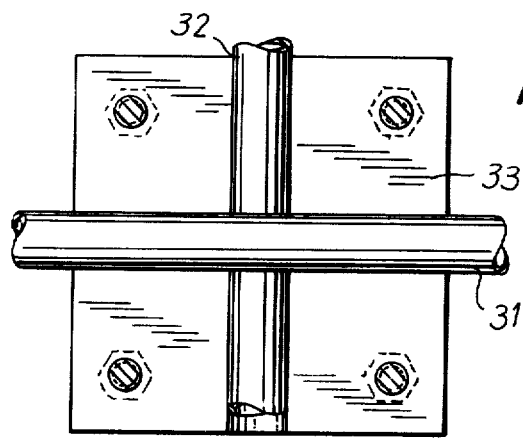
FIGS. 5a and 5b show in plan and cross-section respectively, an arrangement of flexible disposable tubing for use as circuit elements in an apparatus for extracorporeal circulation and treatment of blood.
Figure 5B:
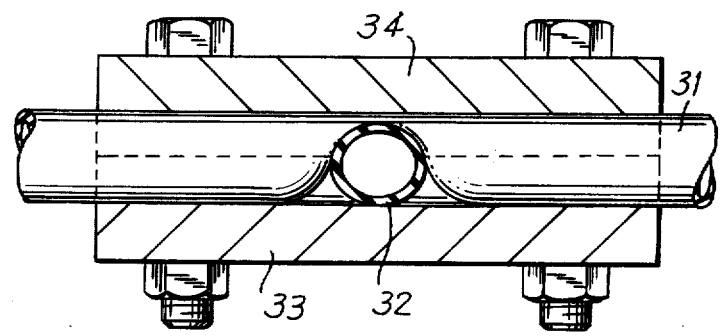

Much the same type of arrangement can be provided through the use of flexible tubing and flexible chambers. Such an arrangement is shown schematically in FIGS. 5a and 5b. Two flexible tubes 31 and 32 are laid in cross channels in support block 34 and held together by any suitable clamping means as by nuts and bolts. FIG. 5a is a plan view of the system with the upper block 34 removed. FIG. 5b is a sectional view through one of the crossed channels. Pressurization of flexible tube 31 closes tube 32 in exactly the same way as is done with the ducting formed between plastic sheets sealed together in a selected pattern. Pumps can also be formed using combinations of the arrangements shown in FIGS. 4a, 4b, 5a and 5b.

Figure 6:
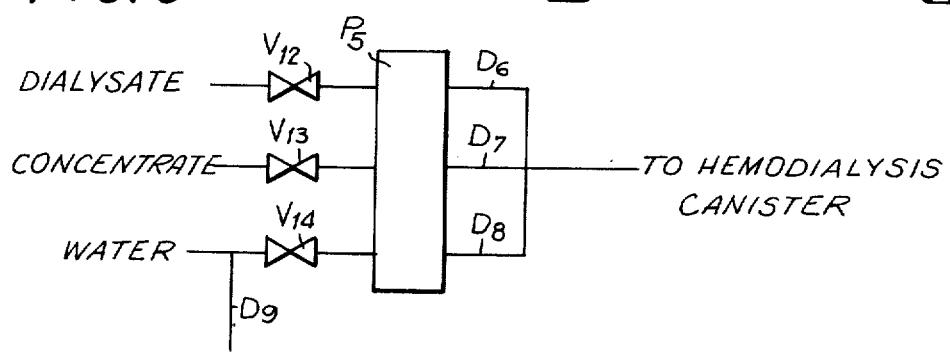
FIG. 6 shows an arrangement of elements for providing either premixed dialysate or mixing concentrate and water prior to supplying same to hemodialysis apparatus.

In carrying out hemodialysis, it may be preferred to use premixed dialysate or, conversely to mix the dialysate from concentrate and water. An arrangement which provides for both possibilities is shown in FIG. 6. Ducts $D_6$, $D_7$ and $D_8$ are of flexible tubing which may be formed, if desired, between sealed-together plastic sheets. All three ducts are subject to manipulation by moving roller or fingers of a pump drive such as has been described above. The relative sizes of the ducts are such that when valves $V_{13}$ and $V_{14}$ are open, dialysate concentrate and water will be supplied in the correct ratio to form dialysate. Conversely, when premixed dialysate is to be supplied to the system, valves $V_{13}$ and $V_{14}$ are closed and valve $V_{12}$ is open; duct $D_6$ is of such a size that the rate of supply of dialysate will be equal to the sum of concentrate and water supplied when valves $V_{13}$ and $V_{14}$ are open. The ducts are brought to a junction through which dialysate flows to the hemodialysate canister.

Where preselected limits for one controller depend on the instantaneous value of another variable and particularly on the cardiovascular status of the patient, it is desirable that a master controller MC be provided. This master controller takes signals from each controller and, if necessary from sensors as well and then feeds back appropriate signals to selected controllers to change the preselected limits, within which selected controllers are to operate. The master controller may be preprogrammed to change said limits in accordance with the functions being carried out by the system or dynamically in response to the condition of the patient. Thus, an increase in the pulse rate of the patient without a decrease in blood pressure calls for a decrease in the pressure difference across the ultrafiltration membrane to decrease the rate of ultrafiltration. An increase in pulse rate accompanied by a decrease in blood pressure within limits acceptable for automatic compensation calls for a decrease in rate of withdrawal of blood from the patient as well as a drop in ultrafiltration rate to reestablish an acceptable set of operating conditions.

Further, said MC may be constructed to accept programs designed for specific individuals or specific conditions. Thus when attaching a patient to apparatus in accordance with the present invention, insertion of a tape, or punch card or cassette or the like may suffice to adjust all limits for variables and the relationships between them, as well as the course of the necessary treatment. The relationship of the master controller to the subordinate controllers $C_1, C_2, C_3 \ldots$, and sensors is shown schematically in FIG. 7. A signal is transmitted from each subordinate controller to MC which then adjusts the limits for each of the related variables according to either internal programming or programming desired for the specific patient and/or treatment.

FIG. 8 shows in perspective an embodiment of the invention in which the principal sections of the apparatus are mounted in appropriately shaped recesses in a back wall. In the embodiment shown, all of the pumps in the apparatus are driven by a single motor through a roller or fingers. This arrangement is particularly convenient in that it provides synchronous pumping. Fixed pumping ratios, where needed, are established by choice of the relative sizes of the tubing or ducting acted on by the roller or fingers. Also, these ratios are held constant even when conditions call for increasing or decreasing the blood flow rate. In sizing the tubing it should be noted that the blood flow rate usually is in the range of 0–500 cc/min. and the dialysate flow rate is usually in the range of 0–1500 cc/min.

The embodiment is also adaptable for incorporation of disposable members formed of tubing or plastic sheet sealed together in appropriate patterns. It will, of course, be realized that the embodiment shown in FIG. 8 is only one of many possible, and the claims are not to be considered as restricted to the embodiment shown.

The master controller also can accept programs specific to individuals or circumstances so that it becomes unnecessary to establish all of the preselected limits each time treatment of a new patient is started.

Preferably, either M or MC should give visible indication as to the status of all variables under control and whether any, and if so, which variable is out of control.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention, which, as a matter of language, might be said to fall therebetween.

What is claimed is:

1. An improved apparatus for receiving blood or other fluid and physiological samples and carrying out diagnostic tests on said blood, fluid and samples, for automated therapeutic infusion, and being particularly suited for automated extracorporeal treatment of blood from a plurality of patients either in sequence or with a plurality of units simultaneously, said apparatus including in spatial sequence blood-taking means for taking blood from a patient, a blood treatment chamber for treating said blood, said treatment including oxygenation and dialysis, and blood returning means, said improvement comprising first sensor, signalling and controller means for holding the rate of taking blood from said patient within programmable limits, second sensor, signalling and controller means for controlling the pressure of said taken blood in said apparatus within programmable limits, third sensor, signalling and master controller means for monitoring the cardiovascular status of the patient, said master controller means being operatively connected to said first and second controller means for adjusting said programmable limits of same to hold said cardiovascular status within limits appropriate to the condition of said patient and the stage and progress of said treatment, and monitor means operatively connected to said first, second and third controller means for detecting divergence of any of said rate of taking of blood, pressure of blood in said apparatus and cardiovascular status of said patient beyond programmed limits for a period of time longer than a preselected period, said monitor means being programmed to shut down said apparatus on detection of such a divergence for said longer than preselected period thereby making said apparatus fail-safe, and making said monitor a fail-safe monitor, the information received by said master controller means from said third sensor means and from said first and second sensor means constituting a system in which said signals from said patient take precedence for shutting down said apparatus even when said first and second sensor means indicate that said apparatus is functioning with programmed limits, thereby establishing the safety and well-being of the patient as the dominating variable.

2. The apparatus as defined in claim 1 wherein said master controller is adapted to be programmed for treatment of specific patients or conditions.

3. The improved apparatus as defined in claim 1, further comprising a disposable flexible component including reaction and observation chambers, reservoirs for storing reagents, and passages connecting said chambers and reservoirs and said blood-taking means; and means for automatically transferring a fluid sample taken from an individual through said passages and into said reaction chamber in which a reagent is stored and into said observation chamber for examination optionally before or after being subjected to chemical reaction, provision being made for optionally dividing said sample into portions each of which can be subjected to a different reaction and observed by different means, said apparatus being such that it can be programmed to carry out said reactions and observations automatically and rapidly enough to utilize the results obtained therefrom in the treatment of blood being treated simultaneously.

4. The apparatus as defined in claim 1, wherein said apparatus further comprises means for transferring oxygen from a gas consisting at least in part of oxygen into said blood.

5. The improved apparatus as defined in claim 1, wherein said third sensor, signalling and master controller means includes EKG-monitoring means and said fail-safe monitor means is adapted to shut down said apparatus if said master controller means indicates that the cardiovascular status of said patient remains outside programmed limits for longer than a preselected period of time.

6. The improved apparatus as defined in claim 1, further comprising a bubble trap means in said blood-returning means, fifth sensing means, signalling and controller means for sensing and controlling the level of blood in said bubble trap means, and first flow-rate adjusting means in said blood returning means, said first flow-rate adjusting means being controlled by said fifth controller means for holding said blood level in said trap means within programmed limits.

7. The apparatus as defined in claim 6, further comprising vent means in said bubble trap and eighth sensing signalling and controlling means for measuring and controlling the pressure in said bubble trap by opening said vent means to release gas from above the level of liquid in said bubble trap, said eighth controller means being operatively connected with said fail-safe monitor for shutting down said apparatus in the event the pressure in said bubble trap deviates beyond programmed limits for longer than a preselected period.

8. The improved apparatus as defined in claim 6, further comprising a saline reservoir under the control of said fifth controller means and connected to said bubble trap means for adding saline to said bubble trap means in the event of a sudden drop in liquid level in said trap, said fifth controller means being adapted to signal said fail-safe monitor to shut down said apparatus in the event that activation of said first flow-rate adjusting means and addition of saline fail to return said liquid level to within preselected limits within a preselected period of time.

9. The improved apparatus as defined in claim 8, further comprising second flow-rate adjusting means in said blood-taking means, sixth sensing, signalling and controller means connected with said second flow-rate adjusting means for holding the rate of blood-taking within programmable limits, said sixth controller means being under the control of said master controller means for adjusting said programmable limits in accordance with the cardiovascular state of said patient and the stage of blood treatment in progress and for signalling said fail-safe monitor to shut down said apparatus in the event that the cardiovascular state of said patient deviates outside said programmable limits for a period in excess of a preselected period.

10. The improved apparatus as defined in claim 1, further comprising seventh sensing, signalling and controller means, and pressure-adjusting means operatively connected with said blood treatment chamber, said seventh controller means being connected with said pressure-adjusting means for holding the pressure in said blood-treatment chamber within programmable limits, said programmable limits being under the control of and adjustable by said master controller in accordance with the condition of said patient and the progress of said treatment of said blood, said seventh controller means being adapted for signalling said fail-safe monitor to shut down said apparatus in the event that said pressure of blood in said blood-treatment chamber deviates outside said programmable limits for longer than a preselected period of time.

11. The improved apparatus as defined in claim 1, wherein said blood-returning means includes first flow-rate adjusting and measuring means and said blood-taking means includes second flow-rate adjusting and measuring means.

12. The apparatus as defined in claim 11, wherein at least said one of said flow-rate adjusting means includes flexible tubing, thereby making it possible to control the rate of flow of blood therethrough by selective and controlled compression of the wall of said tubing.

13. The apparatus as defined in claim 11, wherein at least one of said flow-rate adjusting means includes a first pair of flexible plastic sheets sealed together in an appropriate pattern including duct and pump means thereby making it possible to control the rate of flow of blood through said duct means by selective and controlled compression of the walls of said duct means.

14. The apparatus as defined in claim 13, wherein at least one of said pump and duct means is formed between said first pair of flexible plastic sheets and further comprising at least a second pair of flexible plastic sheets having appropriately shaped channels formed therebetween, said channels being connectable to pneumatic controls, said second pair of sheets being contiguous with said first pair so that selective pressurization of said channels by said pneumatic controls selectively compressing walls of said duct means, whereby the combination of said first and second pairs of plastic sheets with said pneumatic controls constitutes at least one of said pump means and said duct means.

15. The improved apparatus as defined in claim 1, wherein said blood-returning means and said blood-taking means each include a normally-closed valve so that a power failure will result in shutting down said apparatus and isolating said patient.

16. The improved apparatus as defined in claim 1, wherein said third sensor, signalling and master controller means includes means for monitoring the blood pressure and pulse rate of said patient and said fail-safe monitor means is adapted to shut down said apparatus if said master controller means indicates that the cardiovascular status of said patient remains outside programmed limits for longer than a preselected period of time.

17. The improved apparatus as defined in claim 16, wherein said patient has an arterio-venous fistula and said third sensor means monitors the pressure in said fistula as a means of determining the blood pressure of said patient.

18. The improved apparatus as defined in claim 1, wherein said apparatus is adapted for feeding anticoagulant at a controlled ratio into the blood taken by said blood-taking means.

19. The apparatus as defined in claim 1, wherein said fail-safe monitor is programmed to activate an alarm on shutting down said apparatus.

20. The apparatus as claimed in claim 1, including data display for indicating status of patient and treatment.

21. The apparatus as claimed in claim 1, further comprising means for adding medicaments to said blood.

22. The apparatus as defined in claim 1, wherein said treatment consists of dialysis for removal of excess water and solutes from said blood by ultrafiltration and mass action and said treatment chamber has therein a semi-permeable membrane dividing said chamber into a blood compartment and a dialysate compartment, each having ducts for entrance and exit respectively of blood and of dialysate, and further comprising fourth sensing, signalling and controller means for controlling the rate of flow of dialysate and the pressure difference and the rate of transfer of fluid and solutes across said membrane, between programmed limits said fourth controller means being connected to said master controller means for adjusting said programmed limits in accordance with established relationships among said operating conditions including the relative rates of flow of blood and dialysate, the pressure difference and the rate of transfer of fluid across said membrane, the cardiovascular status of said patient and the stage and progress of said dialysis, and being operatively connected to said fail-safe monitor means for shutting down said apparatus in the event that any of said operating conditions deviates beyond a programmed limit for a preselected period of time during which said controller means are programmed to return said deviated operating condition to within said programmed limits.

23. The apparatus as defined in claim 22, further comprising third and fourth measuring means for measuring the rate of flow of dialysate entering and leaving the dialysate chamber respectively and integrating means operatively connected with said third and fourth flow-rate measuring means so that the total volume of water removed up to any time during treatment of blood from a patient may be determined.

24. The apparatus as defined in claim 23, wherein said integrating means includes an essentially vertical vessel of known volume, having a top and a bottom, vessel level sensing means proximate the top of said vessel for sensing and signalling the accumulated volume of fluid, dump means proximate the bottom thereof, dump control means for activating said dump means on receiving a signal from said vessel level sensing means and counter means for recording the number of times said vessel has been filled and emptied, said vessel being positioned for collecting fluid leaving said dialysate compartment.

25. The apparatus as defined in claim 22, further comprising means for selectively supplying premixed dialysate and means for mixing water and dialysate concentrate in appropriate ratio to form and supply dialysate.

26. The apparatus as defined in claim 22 further comprising means for separating and recovering a portion of the water from the dialysate leaving the blood treatment chamber, and ducting for recirculating said water for combination with fresh dialysate concentrate, said water being essentially free of organic waste products.

27. The apparatus as defined in claim 22, wherein said apparatus includes means for detecting blood in the stream of dialysate leaving said blood-treatment chamber, said blood-detecting means being operatively connected with said fail-safe monitor means for shutting down said apparatus in the event that blood in an amount greater than a preprogrammed limit is detected in said stream.

28. The apparatus as defined in claim 22, wherein said master controller means is preprogrammed so that on detection of an increase in the pulse rate of the patient in the absence of a decrease in blood-pressure, said fourth controller means is adjusted to decrease the pressure difference across said membrane to decrease the rate of ultrafiltration and on detection of an increase in pulse rate in combination with a decrease in blood pressure said first controller means is adjusted to decrease the rate of withdrawal of blood from said patient and said fourth controller means is adjusted to decrease the pressure difference across said membrane.

29. The apparatus as defined in claim 22, further comprising fifth controller means for adding saline to said bubble trap, said fifth controller means being under the control of said master controller means, and wherein said master controller means is preprogrammed so that on detection of a drop in the blood pressure of said patient below a programmed limit, firstly, said first controller means is adjusted to decrease the rate of withdrawal of blood from said patient, secondly, said fourth controller means is adjusted to decrease the rate of ultrafiltration, and in the event that said blood-pressure does not return to within said programmed limits within a preset period, thirdly said master controller means activates said fifth controller means to add saline to said blood, and in the event that said blood-pressure does not return to within said programmed limits within a second preset period, said master controller means activates said fail-safe monitor to shut down said apparatus.

* * * * *